(12) United States Patent
Sima et al.

(10) Patent No.: US 11,682,482 B2
(45) Date of Patent: Jun. 20, 2023

(54) METHOD AND APPARATUS FOR DETERMINING PSYCHOLOGICAL COUNSELING TRAINING SCHEME

(71) Applicant: Nanjing Silicon Intelligence Technology Co., Ltd., Jiangsu (CN)

(72) Inventors: Huapeng Sima, Jiangsu (CN); Bingtao Hua, Jiangsu (CN); Yiping Tang, Jiangsu (CN); Cheng Wang, Jiangsu (CN)

(73) Assignee: Nanjing Silicon Intelligence Technology Co., Ltd., Jiangsu (CN)

( * ) Notice: Subject to any disclaimer, the term of this patent is extended or adjusted under 35 U.S.C. 154(b) by 0 days.

(21) Appl. No.: 17/594,499

(22) PCT Filed: Jul. 8, 2021

(86) PCT No.: PCT/CN2021/105287
§ 371 (c)(1),
(2) Date: Dec. 29, 2021

(87) PCT Pub. No.: WO2022/166110
PCT Pub. Date: Aug. 11, 2022

(65) Prior Publication Data
US 2022/0277833 A1  Sep. 1, 2022

(30) Foreign Application Priority Data
Feb. 2, 2021  (CN) .......................... 202110141410.8

(51) Int. Cl.
*G16H 20/70* (2018.01)
*G16H 50/70* (2018.01)
*G06N 20/00* (2019.01)

(52) U.S. Cl.
CPC ............. *G16H 20/70* (2018.01); *G06N 20/00* (2019.01); *G16H 50/70* (2018.01)

(58) Field of Classification Search
CPC ......... G16H 20/70; G16H 50/70; G06N 20/00
See application file for complete search history.

(56) References Cited

U.S. PATENT DOCUMENTS

| | | | |
|---|---|---|---|
| 2018/0096738 A1* | 4/2018 | Moturu ................. | G16H 50/20 |
| 2020/0118458 A1* | 4/2020 | Shriberg ................ | G10L 25/66 |

(Continued)

FOREIGN PATENT DOCUMENTS

| | | | |
|---|---|---|---|
| CN | 111180043 A | 5/2020 |
| CN | 111370113 A | 7/2020 |

(Continued)

OTHER PUBLICATIONS

Notification of the First Office Action for Chinese counterpart application 202110141410.8, dated Mar. 15, 2021 (English translation).

(Continued)

*Primary Examiner* — Jonathan Ng
*Assistant Examiner* — Benjamin L. Hanks
(74) *Attorney, Agent, or Firm* — K&L Gates LLP

(57) ABSTRACT

Embodiments of the present disclosure provide a method and apparatus for determining a psychological counseling training scheme. The method includes: obtaining training feeling data of a user after each session of psychological counseling training through an interactive inquiry with the user; inputting the training feeling data into a first classification model, identifying a training result of the user after each session of psychological counseling training by using the first classification model, and collecting statistics about a training result of the user in a current training period; and determining a training scheme of the user for a next training period based on the training result in the current training period of the user. The invention resolves the problem that a counseling result is not ideal because individual demands (Continued)

of different users cannot be satisfied if a psychological robot performs psychological counseling on the user according to a preset counseling procedure.

10 Claims, 5 Drawing Sheets

(56) References Cited

U.S. PATENT DOCUMENTS

2020/0152330 A1* 5/2020 Anushiravani ...... G06V 30/274
2020/0342348 A1 10/2020 Kenny et al.
2021/0383802 A1 12/2021 Li et al.

FOREIGN PATENT DOCUMENTS

| CN | 111666396 A | 9/2020 |
| CN | 111797320 A | 10/2020 |
| CN | 112086169 A | 12/2020 |
| CN | 112270973 A | 1/2021 |
| CN | 112466434 A | 3/2021 |

OTHER PUBLICATIONS

Notification of the Second Office Action for Chinese counterpart application 202110141410.8, dated Apr. 7, 2021 (English translation).
Notification on Grant of Patent Right for Invention for Chinese counterpart application 202110141410.8, dated Apr. 15, 2021 (English translation).
International Search Report and Written Opinion for International Application No. PCT/CN2021/105287 dated Oct. 27, 2021.
Notification of the First Office Action for Chinese counterpart application 202110141410.8, dated Mar. 15, 2021.
Notification of the Second Office Action for Chinese counterpart application 202110141410.8, dated Apr. 7, 2021.
Notification on Grant of Patent Right for Invention for Chinese counterpart application 202110141410.8, dated Apr. 15, 2021.

* cited by examiner

METHOD AND APPARATUS FOR DETERMINING PSYCHOLOGICAL COUNSELING TRAINING SCHEME

This application is a U.S. National Stage Entry under 35 U.S.C. § 371 of International Patent Application No. PCT/CN2021/105287, entitled METHOD AND APPARATUS FOR DETERMINING PSYCHOLOGICAL COUNSELING TRAINING SCHEME, filed Jul. 8, 2021, which claims priority to and the benefit of Chinese Application No. 202110141410.8, filed with the Chinese Patent Office on Feb. 2, 2021 and entitled "METHOD AND APPARATUS FOR DETERMINING PSYCHOLOGICAL COUNSELING TRAINING SCHEME", the entire disclosures of which are incorporated by reference in their entirety herein.

FIELD OF THE INVENTION

The present disclosure relates to the technical field of psychological robots, and in particular, to a method and apparatus for determining a psychological counseling training scheme.

BACKGROUND OF THE INVENTION

A psychological robot is a product that performs psychological therapy/counseling on a user based on artificial intelligence. During use, the psychological robot can determine a psychological problem of the user based on selections of the user or interactions with the user, so as to perform psychological therapy or counseling on the user in an appropriate way. The user can adjust the psychological problem thereof without assistance of a third party, such as a psychologist.

In the prior art, in application scenarios involving interactions with a user within a certain period, interactions with the user usually are completed according to a preset fixed procedure or by using a fixed strategy. Such interaction manner has some drawbacks. During a process in which the psychological robot performs psychological therapy/counseling, because practice effects of users vary from person to person, it is possible that the user does not achieve expected practice effects when the current time period ends. However, at beginning of a next time period, the psychological robot still makes the user perform a next stage of corresponding practices according to an originally set strategy. In this case, not only expected effects cannot be achieved for the user, but also a negative feedback from the user may be caused. As a result, the user may terminate the entire psychological therapy/counseling procedure in advance. In another aspect, a frequency of the user of using the psychological robot is also difficult to be fixed. For example, according to the preset procedure, the user needs to complete at least seven practices in the current time period. If the user actually only practices for one time in the current time period, expected practice effects also cannot be achieved when the current time period ends. In this state, making the user perform a next stage of corresponding practices according to an original strategy also affects subsequent practice effects of the user and overall therapy/counseling effects.

Regarding a problem in the prior art that a counseling result is not ideal because individual demands of different users cannot be satisfied if the psychological robot performs psychological counseling on the user according to a preset counseling procedure, there is no effective solution at present.

SUMMARY OF THE INVENTION

The present disclosure provides a method and apparatus for determining a psychological counseling training scheme, to at least resolve a problem in the prior art that a counseling result is not ideal because individual demands of different users cannot be satisfied if a psychological robot performs psychological counseling on the user according to a preset counseling procedure.

An embodiment of the present disclosure provides a method for determining a psychological counseling training scheme, including: obtaining training feeling data of a user after each session of psychological counseling training through an interactive inquiry with the user, wherein the training feeling data is used to indicate feeling of the user after the psychological counseling training; inputting the training feeling data into a first classification model, identifying a training result of the user after each session of psychological counseling training by using the first classification model, and collecting statistics about a training result of the user in a current training period, wherein the first classification model is a model obtained by training an initial ultra-long text classification model; and determining a training scheme of the user for a next training period based on the training result in the current training period of the user.

An embodiment of the present disclosure further provides an apparatus for determining a psychological counseling training scheme, including: an obtaining module, configured to obtain training feeling data of a user after each session of psychological counseling training through an interactive inquiry with the user, wherein the training feeling data is used to indicate feeling of the user after the psychological counseling training; a processing module, configured to input the training feeling data into a first classification model, identify a training result of the user after each session of psychological counseling training by using the first classification model, and collect statistics about a training result of the user in a current training period, wherein the first classification model is a model obtained by training an initial ultra-long text classification model; and a determining module, configured to determine a training scheme of the user for a next training period based on the training result in the current training period of the user.

An embodiment of the present disclosure further provides a computer-readable storage medium, wherein the storage medium stores a computer program, and the computer program is configured to implement steps in any one of the foregoing method embodiments while being executed.

An embodiment of the present disclosure further provides an electronic device, including a memory and a processor, wherein the memory stores a computer program, and the processor is configured to execute the computer program to implement steps in any one of the foregoing method embodiments.

According to the embodiments of the present disclosure, the training feeling data of the user after each session of psychological counseling training is obtained through the interactive inquiry with the user; the training feeling data is input into the first classification model, the training result of the user after each session of psychological counseling training is identified by using the first classification model, and statistics about the training result in the current training period of the user is collected; and the training scheme of the user for the next training period is determined based on the training result in the current training period of the user. In this case, the following problem is resolved: the counseling result is not ideal because individual demands of different users cannot be satisfied if the psychological robot performs psychological counseling on the user according to the preset counseling procedure. During a process in which the psychological robot performs psychological therapy/counseling on the user, after each time period ends, whether the user achieves expected practice effects is determined based on a practice status of the user. A strategy at a next stage is adjusted based on an actual status of the user, so that the user achieves expected practice effects at each stage. In this way, overall therapy/counseling effects of the user and dependence on the psychological robot are both improved.

DETAILED DESCRIPTION OF THE EMBODIMENTS

The present disclosure is described in detail below with reference to the accompanying drawings and the embodiments. It should be noted that the embodiments in the present disclosure and features in the embodiments can be combined with each other if there is no conflict.

It should be noted that terms "first", "second", and the like in this specification, claims, and accompanying drawings of the present disclosure are intended to distinguish between similar objects, but are not necessarily intended to describe a particular sequence or a sequential order.

Figure 1:
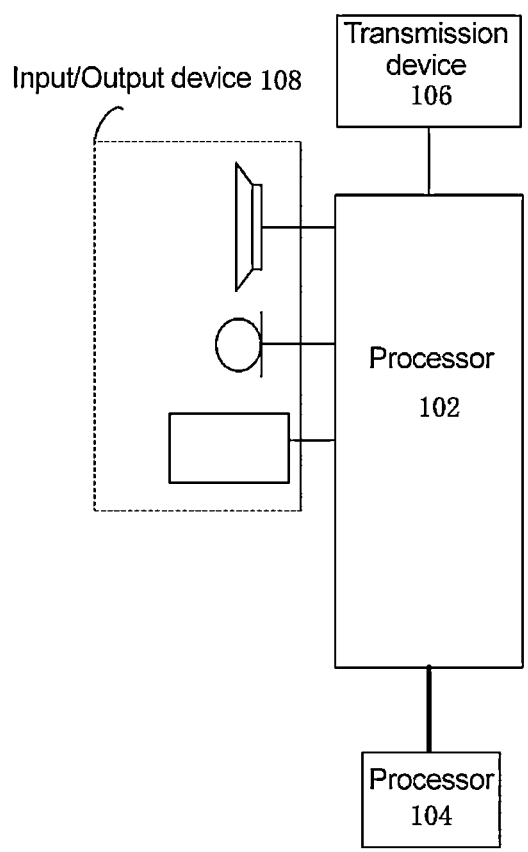
FIG. 1 is a hardware structural block diagram of a mobile terminal of a method for determining a psychological counseling training scheme according to an embodiment of the present disclosure.

Method embodiments provided in the embodiments of the present disclosure can be implemented in a mobile terminal, a computer terminal, or a similar computing device. Descriptions are made by using an example in which the method embodiments are implemented in a mobile terminal. FIG. 1 is a hardware structural block diagram of a mobile terminal of a method for determining a psychological counseling training scheme according to an embodiment of the present disclosure. As shown in FIG. 1, the mobile terminal may include one or more (only one processor is shown in FIG. 1) processors 102 (the processor 102 may include, but is not limited to a processing device such as a microprocessor MCU or a programmable logical device FPGA) and a memory 104 for storing data. The foregoing mobile terminal may further include a transmission device 106 for communications and an input/output device 108. Persons of ordinary skills in the art may understand that the structure shown in FIG. 1 is merely for example, and do not constitute limitation on the structure of the foregoing mobile terminal. For example, the mobile terminal may further include more or less components than those shown in FIG. 1, or may have a configuration different from that shown in FIG. 1.

The memory 104 may be configured to store a computer program, for example, a software program and a module of application software, such as a computer program corresponding to the method for determining a psychological counseling training scheme in this embodiment of the present disclosure. The processor 102 executes the computer program stored in the memory 104 to perform various function applications and data processing, that is, perform the foregoing method. The memory 104 may include a high-speed random access memory, and may further include a non-volatile memory, such as one or more magnetic storage devices, a flash memory, or another non-volatile solid-state memory. In some embodiments, the memory 104 may further include memories remotely disposed with respect to the processor 102, and these remote memories may be connected to the mobile terminal through a network. Examples of the foregoing network include, but are not limited to, the internet, an intranet, a local area network, a mobile communications network, and combinations thereof.

The transmission device 106 is configured to receive or send data through a network. Specific examples of the foregoing network may include a wireless network provided by a communication provider of a mobile terminal. In an example, the transmission device 106 includes a network interface controller (NIC), which can be connected to another network device through a base station, to communicate with the internet. In an example, the transmission device 106 may be a radio frequency (RF) module, and is configured to communicate with the internet in a wireless manner.

Figure 2:
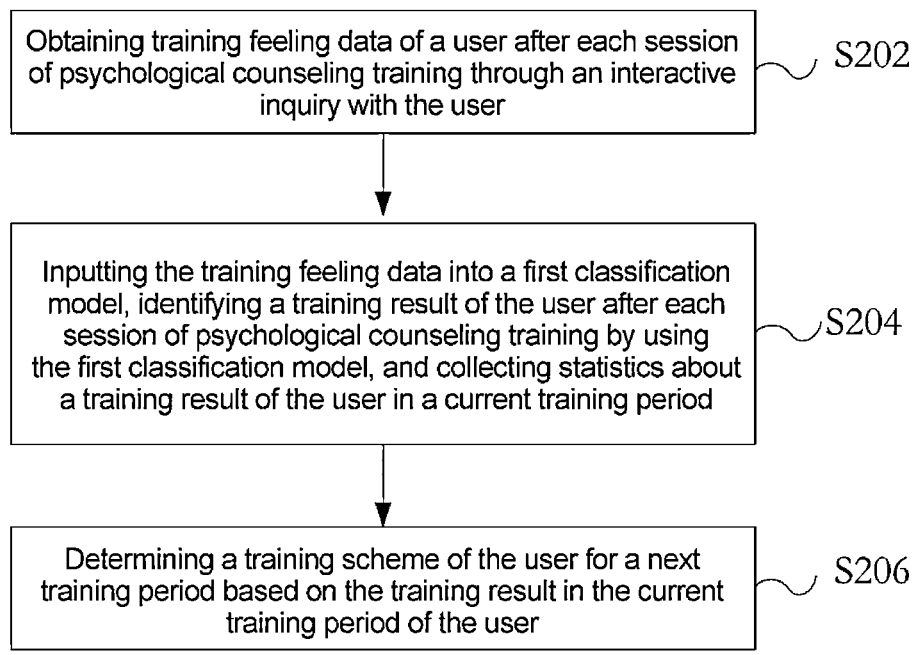
FIG. 2 is a flowchart of an optional method for determining a psychological counseling training scheme according to an embodiment of the present disclosure.

An embodiment of the present disclosure provides a method for determining a psychological counseling training scheme. FIG. 2 is a flowchart of an optional method for determining a psychological counseling training scheme according to an embodiment of the present disclosure. As shown in FIG. 2, the method includes:

Step S202: obtaining training feeling data of a user after each session of psychological counseling training through an interactive inquiry with the user, wherein the training feeling data is used to indicate feeling of the user after the psychological counseling training;

Step S204: inputting the training feeling data into a first classification model, identifying a training result of the user after each session of psychological counseling training by using the first classification model, and collecting statistics about a training result of the user in a current training period, wherein the first classification model is a model obtained by training an initial ultra-long text classification model; and Step S206: determining a training scheme of the user for a next training period based on the training result in the current training period of the user.

The execution body of the method in this embodiment of the present disclosure may be a psychological robot. The psychological robot can be realized by any form of application, for example, an APP, the WeChat applet, or an inherent program carried in a preset terminal. Specifically, an execution terminal involved in the method provided in this embodiment of the present disclosure may include a user terminal and a server, wherein the server may be a cloud server or a local server.

The user terminal is configured to carry the psychological robot and interacts with the user, to perform psychological therapy/counseling on the user. User equipment includes, but is not limited to a mobile phone, a tablet computer, a PC, a wearable device, an indoor large-screen terminal, an outdoor large-screen terminal, and the like.

The server is configured to determine a psychological therapy/counseling approach expected by the user or a psychological therapy/counseling approach suitable for the user based on data input by the user, and subsequently to perform psychological therapy/counseling on the user according to a selected approach.

It should be noted that the training feeling data involved in this embodiment of the present disclosure may include a post-training opinion of the user, post-training body feeling of the user, post-training emotional feeling of the user, and the like. The body feeling may be further specifically classified into: head feeling, shoulder and neck feeling, limb feeling, spine feeling, feeling in core parts of waist and abdomen, or the like. This is not limited in this embodiment of the present disclosure. For example, training feeling data fed back by the user after the training is completed may be:

User opinion: It was so wonderful, and I was much relaxed.

Body feeling: It feels like some parts of the body were disappeared.

Emotional feeling: It feels so good. I seemed to have no weight.

It should be noted that the first classification model may be an ultra-long text classification model that is implemented based on BERT+LSTM, or may be an ultra-long text classification model that is implemented based on BERT+LSTM+CRF, provided that the first classification model is a machine learning model that can achieve natural language recognition and classification. This is not limited in this embodiment of the present disclosure.

In an optional implementation, the foregoing step S204 may be performed according to the following steps:

S1: inputting the training feeling data of the user after each session of psychological counseling training into the first classification model, to generate an N1-dimensional vector corresponding to the training result, wherein each dimension vector in the N1-dimensional vector corresponds to one category of training feeling data, and each dimension vector indicates a training feeling level of the user by using a number;

S2: performing same-position accumulation on N1-dimensional vectors corresponding to multiple training results of the user in the first training period when the user has completed multiple sessions of psychological counseling training in a first training period, to generate an N2-dimensional vector corresponding to the training result of the user in the first training period; and S3: generating an (N2*M)-dimensional vector for a training result in a second training period of the user, wherein M represents a quantity of first training periods contained in each of the second training period.

For example, when the training feeling data includes the post-training opinion of the user, the post-training body feeling of the user, and the post-training emotional feeling of the user, a corresponding 3-dimensional vector (x, y, z) may be generated after the user completes the psychological counseling training for one time, wherein N1=3, and x corresponds to the post-training opinion of the user, y corresponds to the post-training body feeling of the user, and z corresponds to the post-training emotional feeling of the user. The training feeling level may respectively indicate bad feeling, ordinary feeling, and good feeling by using −1, 0, and 1. For example, if a 3-dimensional vector (1, 0, 1) is generated after the user completes one session of psychological counseling training, it indicates that the post-training opinion of the user is good, the post-training body feeling is ordinary, and the post-training emotional feeling is good. Therefore, overall feeling is relatively positive. The training feeling level may alternatively respectively indicate, by using 1, 2, 3, 4, and 5, degrees to which feeling becomes better. For example, 1 means the worst and 5 means the best, or 1 means the best and 5 means the worst. The training feeling level is not limited to the foregoing three or five levels, and can be set according to actual requirements. This is not limited in this embodiment of the present disclosure.

The same-position accumulation described in this embodiment of the present disclosure may be understood as follows. When multiple sessions of psychological counseling training are completed in the first training period, for example, if four sessions of psychological counseling training are completed on a same day (the first training period is one day), 3-dimensional vectors corresponding to the four sessions of psychological counseling training respectively are (x1, y1, z1), (x2, y2, z2), (x3, y3, z3), and (x4, y4, z4). Statistics about total training results on this day may be collected to form a 3-dimensional vector, which is represented as (x1+x2+x3+x4, y1+y2+y3+y4, z1+z2+z3+z4). If the user does not provide result feedback after a certain training session, a current 3-dimensional vector may be set as a default vector, for example, (0, 0, 0).

The second training period may be understood as a therapy/counseling course, for example, one week (seven days). In the whole second training period, if the user does not perform training on one day, or does not provide training result feedback, a 3-dimensional vector of this day may be set as a default vector, for example, (0, 0, 0). After training in the whole second training period is completed, vectors in the second training period are integrated to form a (3*7)-dimensional vector, that is, a 21-dimensional vector.

In an optional implementation, before the step of inputting the training feeling data of the user after each session of psychological counseling training into the first classification model to generate the N1-dimensional vector corresponding to the training result, the foregoing method further includes:

S1: obtaining a first sample data, wherein the first sample data includes at least one of the following categories: data used to describe a post-training idea, data used to describe post-training body feelings, and data used to describe post-training emotional feeling;

S2: annotating a training feeling level of each category of the first sample data; and S3: training the first classification model by using the annotated first sample data, wherein different categories of the first sample data are used to correspondingly train different categories of the first classification models.

It should be noted that the first classification model may collect a first sample data of the user that is related to opinions, body feeling, and emotional feeling of the user before training the model or during a process of training the module. Moreover, the foregoing sample data may be annotated by a psychologist, or the sample data is clustered and annotated after keywords are identified by using a computer. For example, 1 is used to indicate that a tendency is getting better, 0 is used to indicate that the tendency is no change, and −1 is used to indicate that the tendency is getting worse. For a case in which the user does not provide feedback, an annotation may be made by using 0.

The annotated first sample data is input into the initial ultra-long text classification model for training. It should be noted that a classification model is trained separately for each category of training feeling data. For example, the first sample data for describing post-training opinions may be used to train a classification model for the post-training opinion of the user; the data for describing post-training body feeling may be used to train a classification model for the post-training body feeling of the user; and the data for describing post-training emotional feeling may be used to train a classification model for the post-training emotional feeling of the user. Structures of the foregoing a plurality of classification models may be the same or different.

In an optional implementation, after generating an (N2*M)-dimensional vector for the training result in the second training period of the user, the method further includes:

counting a quantity of training sessions of the user that are completed in the second training period, to serve as an (N2*M+1)-dimensional vector.

It should be noted that the psychological robot or the server can count a quantity of practices of the user, that is, collect statistics about frequency in the second training period of the user. In an example, during the second training period that lasts for one week, if the user completes two practices every day on Monday, Wednesday, Friday and Sunday, and completes one practice every day on Tuesday, Thursday and Saturday, at the end of the week, it may be recorded that the user practices for 11 times in total, and 11 may serve as a $22^{th}$-dimensional vector.

In an optional implementation, the foregoing step S206 may be performed according to the following steps:

S1: obtaining, through an interactive inquiry with the user, a feedback result of the user after the current second training period ends;

S2: determining a training scheme of the user for a next second training period according to a preset training procedure when the feedback result of the user indicates that expected effects are achieved; and S3: inputting the training result in the current second training period of the user into a second classification model when the feedback result of the user indicates that expected effects are not achieved or the user does not explicitly provide feedback, and determining the training scheme of the user for the next second training period by using the second classification model, wherein the second classification model is a model obtained by training an initial classifier model.

It should be noted that after each second training period (for example, one week) ends, the psychological robot queries the user for a summary about practices performed in the current second training period. In an example, if the user expresses that expected practice effects are achieved in the current second training period, for example, the user expresses that "Practice effects in this week are very good, and it feels like my initial goal has been reached", a next stage of practices is performed in a next time period according to the preset procedure. In another example, if the user does not explicitly express that expected practice effects are achieved in the current period, for example, the user expresses that "It seems that my training in this week is ordinary", "It seems that my initial goal is not reached", or the like, or if the user fails to provide feedback to the inquiry of the psychological robot, a training mode suitable for a next stage of the user is predicted by using the pre-trained second classification model based on a practice status, about which statistics is collected, of each practice of the user in the current second training period and a practice quantity of the user, so as to adjust a training strategy for a next stage of the user.

It should be noted that the second classification model may be an SVM classifier. Training and a prediction speed of the SVM classifier are more efficient than those of a classification model based on deep learning. Meanwhile, training data of the SVM classifier are processed features, involving no semantic information. A feature vector output by the first classification model may be directly used as input data. In this embodiment of the present application, by using the SVM classifier, prediction efficiency of the second classification model may be improved and the overall model is lightened under a premise of realizing functions of the second classification model.

In an optional implementation, the step of inputting the training result in the current second training period of the user into the second classification model, and determining the training scheme of the user for the next second training period by using the second classification model may be performed according to the followings steps:

S1: inputting an L-dimensional vector corresponding to statistics of the user in the current second training period into the second classification model, wherein the L-dimensional vector includes an (N2*M)-dimensional vector corresponding to the training result in the current training period of the user or an (N2*M+1)-dimensional vector corresponding to the training result and a quantity of training sessions of the user in the current training period;

S2: outputting a psychological tendency result of the user by using the second classification model, wherein the psychological tendency result is used to indicate whether the training of the user in the current second training period achieves expected effects; and S3: determining the training scheme of the user for the next second training period based on the psychological tendency result of the user.

It should be noted that the feature vector input to the second classification model may be the (N2*M)-dimensional vector corresponding to the training result in the current training period of the user, or may be the (N2*M+1)-dimensional vector that contains the quantity of training sessions. A dimension of a vector processed by the second classification model is consistent with a dimension of the L-dimensional vector. When input data does not contain a counted quantity, a processing dimension of the second classification model is N2*M dimensions. When input data contains the counted quantity, the processing dimension of the second classification model is N2*M+1 dimensions. For example, when the feature vector input to the second classification model is a 21-dimensional vector, the corresponding second classification model is a model that processes a 21-dimensional vector. When the feature vector input to the second classification model is a 22-dimensional vector, the corresponding second classification model is a model that processes a 22-dimensional vector.

In an optional implementation, before determining the training scheme of the user for the next second training period by using the second classification model, the second classification model may be trained in the following manners:

S1: obtaining second sample data composed of an L-dimensional vector corresponding to statistics of the user in a second training period;

S2: annotating a psychological tendency result corresponding to the second sample data, wherein the psychological tendency result includes at least one of the following: satisfaction and dissatisfaction; and S3: training the second classification model by using the annotated second sample data.

Taking the SVM classifier as an example, a pre-training is required, wherein 21-dimensional vectors or 22-dimensional vectors obtained by different users or obtained by the user in different training periods are taken as sample data. The second sample data is annotated by a psychologist, or the sample data is annotated by a computer by means of identifying keywords using a machine learning algorithm. An annotation manner may be using 1 to indicate that the tendency is feeling satisfied, and using −1 to indicate that it is felt ordinary or dissatisfied. Alternatively, five levels of 1 to 5 may be used to indicate satisfaction degrees, wherein 1 indicates the most dissatisfied, 5 indicates the most satisfied, and the like. If the annotated category is more detailed, a strategy adjusted by the psychological robot is more close to requirements of the user. This is not limited in this embodiment of the present disclosure. Subsequently, a trained SVM classifier may be obtained by inputting the annotated sample data into the SVM classifier for training.

In an optional implementation, when the feedback result of the user indicates that expected effects are achieved, the method further includes:

obtaining a target L-dimensional vector corresponding to statistics of the user in the current second training period;

annotating a psychological tendency result corresponding to the target L-dimensional vector as satisfaction; and inputting the annotated target L-dimensional vector into the second classification model for training, and updating the second classification model.

When the user explicitly expresses that expected practice effects are achieved in the current training period, the L-dimensional vector corresponding to the statistics may be annotated as 1 to indicate satisfaction, and the annotated L-dimensional feature vector may be input into the SVM classifier for training, to update the SVM classifier. In this way, as the user constantly uses the psychological robot, the SVM classifier is continuously updated to have more accurate prediction effects.

The following describes an implementation process of an optional method for determining a psychological counseling training scheme according to embodiment of the present disclosure by using a specific example.

In S11, every time after the user completes a practice, the psychological robot inquires the user about training feeling. The inquiry process may include the following questions: a post-training opinion of the user, post-training body feeling of the user, post-training emotional feeling of the user, and the like.

It should be noted that the foregoing inquiry may be performed in the following manner: directly inputting by the user through text or voice after a question is proposed to the user; or providing the user with options such as text/rating, so that the user provides feedback through a tap operation. The following table shows content fed back by a plurality of users.

| User | Thought | Body feeling | Emotional feeling |
| --- | --- | --- | --- |
| User 001 | It was so wonderful, and I was much relaxed | It feels like some parts of the body were disappeared. | It feels so good, and I seemed to have no weight. |
| User 002 | I cannot help making blind and disorderly conjectures. | | I was so frustrated that I cannot gain anything from the practice. |
| User 003 | | I tried to relax, but I kept noticing that may body is nervous and painful. | I found myself in tears, but I did not know why. |
| . . . | | | |

In S12, the user provides feedback about the questions in S11. After receiving the feedback of the user, the psychological robot identifies the foregoing user feedback by using a pre-trained classification model (equivalent to the foregoing first classification model), to evaluate a user status of this practice. Correspondingly, every time after the user completes a practice, the psychological robot needs to record a user status of the practice at this time, and also needs to count a quantity of practices of the user.

It should be noted that the foregoing classification model is an ultra-long text classification model that is implemented based on BERT+LSTM.

According to the foregoing annotating rule, after the feedback of a plurality of users in the table above is identified, it may be that:

| User | Thought | Label | Body feeling | Label | Emotional feeling | Label |
| --- | --- | --- | --- | --- | --- | --- |
| User 001 | It was so wonderful, and I was much relaxed~ | 1 | It feels like some parts of the body were disappeared. | 1 | It feels so good, and I seemed to have no weight. | 1 |
| User 002 | I cannot help making blind and disorderly conjectures. | −1 | | 0 | I was so frustrated that I cannot gain anything from the practice. | −1 |
| User 003 | | | I tried to relax, but I kept noticing that may body is nervous and painful. | 0 | I found myself in tears, but I did not know why. | −1 |
| . . . | | | | | | |

In this way, (1, 1, 1) may be used to express a status of this practice of the user 001; (−1, 0, −1) may be used to express a status of this practice of the user 002; and (0, −1, −1) may be used to express a status of this practice of the user 003.

Figure 3:
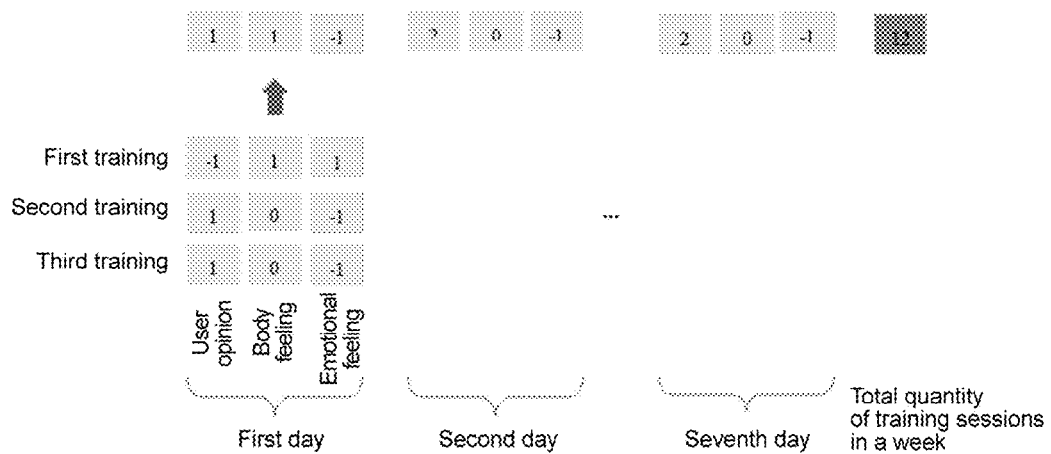
FIG. 3 is a schematic diagram of an optional training result of a user in a whole time period according to an embodiment of the present disclosure.

When the user continues to practice in the current time period, for every practice, a practice status of each practice may be indicated by using a three-dimensional vector similar to the foregoing three-dimensional vector. Taking a certain user as an example, when the user completes an entire time period, a practice status of the user is shown in FIG. 3. FIG. 3 is a schematic diagram of an optional training result of a user in a whole time period according to an embodiment of the present disclosure. As shown in FIG. 3, a practice status of each practice performed by the user every day can be represented by a corresponding three-dimensional vector. By performing same-position accumulation on three-dimensional vectors corresponding to practice statuses of three practices on a first day of the user, a new three-dimensional vector used for representing a practice status of the first day of the user, that is, (1, 1, −1) in FIG. 3, may be obtained. By analogy, a practice status of each day in a week of the user can be determined by performing same-position accumulation on practice statuses recorded after all practices on that day. In this way, seven three-dimensional vectors may be obtained. The seven three-dimensional vectors are aggregated to form a 21-dimensional vector that represents a practice status of this week of the user.

Meanwhile, a quantity of practices performed by the user in this week may be further counted. In FIG. 3, the user has practiced for 12 times in total in this week. In other words, one dimension is added to the 21-dimensional vector, to represent a practice quantity/practice frequency in this week of the user.

In this way, the practice status and the practice quantity in one week of the user may be represented by using a 22-dimensional feature vector. When the user is in any time period, or for any user, a practice status and a practice quantity of the user in a fixed time period both can be recorded according to the foregoing manner.

In S13, after each time period (for example, one week) ends, the psychological robot queries the user for a summary about practices performed in the current time period. In an example, if the user expresses that expected practice effects are achieved in the current time period, for example, the user expresses that "Practice effects in this week are very good, and it feels like my initial goal has been reached", a next stage of practices is performed in a next time period according to the preset procedure. In another example, if the user does not explicitly express that expected practice effects are achieved in the current period, for example, the user expresses that "It seems that my training in this week is ordinary", "It seems that my initial goal is not reached", or the like, or if the user fails to provide feedback to the inquiry of the psychological robot, a training mode suitable for a next stage of the user is predicted by using the pre-trained SVM classifier based on the practice status of each practice of the user that is determined in S12 and a practice quantity of the user, so as to adjust a strategy for a next stage of the user.

It should be noted that the training and a prediction speed of the SVM classifier are more efficient than those of a classification model based on deep learning. Meanwhile, training data of the SVM classifier is processed features, involving no semantic information. Therefore, effects of the SVM classifier are equivalent to those of the classification model based on deep learning.

The foregoing SVM classifier needs to be pre-trained, wherein the 22-dimensional vectors in S12 obtained by different users or by the user in different time periods are taken as sample data, and the sample data is annotated by a psychologist. An annotation manner may be using 1 to indicate that the tendency is feeling satisfied, using −1 to indicate that it is felt ordinary or dissatisfied. A trained SVM classifier may be obtained by inputting the annotated sample data into the SVM classifier for training.

In S13, if the user does not explicitly express that expected practice effects are achieved in the current period, the 22-dimensional feature vector used to represent the practice status and the practice quantity of the user is input into the SVM classifier, and the feature vector is identified by using the SVM classifier to determine a label corresponding to the feature vector. The table below shows labels determined after the SVM classifier identifies based on practice statuses and practice quantities of different users.

| User | Feature vector | Label |
| --- | --- | --- |
| User 001 | 1 −1 3 0 1 0 4 0 −2 2 3 4 1 −1 3 1 2 1 0 1 2 41 | 1 |
| User 002 | 1 2 1 0 0 0 0 0 −1 −1 2 1 0 0 0 0 0 2 1 2 2 25 | 1 |
| User 003 | 0 1 −3 2 −1 −1 −1 2 0 0 0 0 0 1 0 −2 −1 −1 0 0 0 23 | −1 |
| ... | | |

In the table above, identification results of user 001 and user 002 are 1, that is, satisfaction. Therefore, a next stage of practices can be performed for user 001 and user 002 according to the preset procedure. An identification result of user 003 is −1, that is, dissatisfaction. Therefore, for user 003, the practice effects in the current time period are not ideal. In this case, in the next time period, the psychological robot may enable the user to practice again according to the practice mode in the previous stage, or may enable the user to practice according to another practice mode.

Meanwhile, in S13, if the user explicitly expresses that expected practice effects are achieved in the current period, label 1 may be given to the 22-dimensional feature vector used to represent the practice status and the practice quantity of the user. The annotated 22-dimensional feature vector is input into the SVM classifier for training, to update the SVM classifier. In this way, as the user constantly uses the psychological robot, the SVM classifier is continuously updated to have more accurate prediction effects.

The psychological counseling training scheme according to the embodiments of the present disclosure may be provided by a psychological robot. The psychological robot may provide various treatments, including mindfulness treatment, hypnotic therapy, CBT cognitive therapy treatment, relaxation treatment, and the like. Using mindfulness treatment as an example, after a mindfulness treatment manner is determined, the psychological robot provides the user with different mindfulness practice manners every week during an 8-week course of treatment, for example, mindfulness meditation, mindfulness breathing, mindfulness exercises, and mindfulness diet etc. In this way, the user is enabled to get rid of negative emotions by means of mindfulness, thus achieving a purpose of psychological therapy. Limited by personality, independence of living habits, and reasons for impact on psychologies of a user, subjective and objective treatments suitable for the user are different. For example, for a user who is accustomed to relaxing alone and has a regular daily schedule, the mindfulness treatment may have excellent effects; and a user who is accustomed to exercising to relax and lacks of fixed time for meditation every day is not suitable for the mindfulness treatment. For another example, a user who is depressed due to workplace conflicts, disputes, and the like is suitable for the mindfulness treatment; and the mindfulness treatment has relatively limited effects for a user who is mentally exhausted due to excessive physical labor.

Therefore, when the user does not achieve good effects in a treatment period, a next treatment period may be adjusted to have another treatment plan that is more suitable for training habits of the user based on a quantity of practices or a piece of unsatisfactory/non-ideal training feeling data; alternatively, training content of the previous treatment period may be repeated.

According to this embodiment of the present disclosure, during a process in which the psychological robot performs psychological therapy/counseling to the user, whether the user achieves expected practice effects is comprehensively determined after each time period ends, based on a practice status and a quantity of practices of the user and a summary of the user about the practices at this stage when a current time period ends. In this case, when the user does not achieve expected practice effects, psychological therapy/counseling is not performed on the user according to the preset procedure or a predicted strategy, but a strategy in the next stage is adjusted based on an actual status of the user, and the practice of the user at each stage may achieve expected effects. In this way, overall therapy/counseling effects of the user and dependence on the psychological robot are both improved.

The feature application method in the determining and identification process used in the embodiment of the present disclosure not only simply recognizes tendencies of the user, but also makes a certain tendency of the user more prominent by means of same-position accumulation, thereby improving identification accuracy in the identification process, and further adjusting a corresponding strategy according to actual requirements.

According to this embodiment of the present disclosure, the classifier may be retrained and updated during use of the user, so that the identification or determining effects of the psychological robot can be significantly improved as the quantity of users and use time increase.

According to the description of the above implementations, a person skilled in the art may clearly understand that the method according to the foregoing embodiment can be implemented through software in combination with a necessary general hardware platform; and certainly, the method may be implemented by hardware. However, in many cases, the former is a better implementation. On the basis of such understanding, the technical solutions of the present disclosure essentially or parts of the technical solutions of the present disclosure that attribute to the prior art can be represented in software products. A computer software product is stored in the storage medium (such as a ROM/RAM, a magnetic disk, or a compact disc), and includes a plurality of instructions to enable a terminal device (which may be a mobile phone, a computer, a server, a network device, or the like) to perform the method in various embodiments of the present disclosure.

Figure 4:
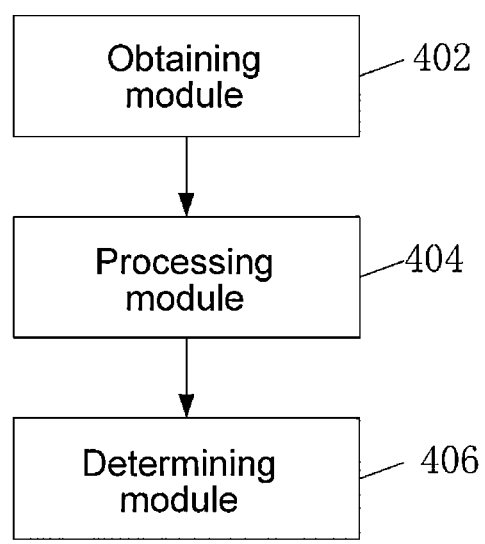
FIG. 4 is a structural block diagram of an optional apparatus for determining a psychological counseling training scheme according to an embodiment of the present disclosure.

According to another aspect of an embodiment of the present disclosure, an apparatus for determining a psychological counseling training scheme for implementing the foregoing method for determining a psychological counseling training scheme is further provided. The device is configured to implement the foregoing embodiment and preferred implementations, and those have been described are not described again. As used below, the term "module" can implement a combination of software and/or hardware with predetermined functions. Although the device described in the following embodiment is preferably implemented by software, the implementation of hardware or a combination of software and hardware is also possible and is conceived. FIG. 4 is a structural block diagram of an optional apparatus for determining a psychological counseling training scheme according to an embodiment of the present disclosure. As shown in FIG. 4, the apparatus includes:

an obtaining module 402, configured to obtain training feeling data of a user after each session of psychological counseling training through an interactive inquiry with the user, wherein the training feeling data is used to indicate feeling of the user after the psychological counseling training;

a processing module 404, configured to input the training feeling data into a first classification model, identify a training result of the user after each session of psychological counseling training by using the first classification model, and collect statistics about a training result of the user in a current training period, wherein the first classification model is a model obtained by training an initial ultra-long text classification model; and a determining module 406, configured to determine a training scheme of the user for a next training period based on the training result in the current training period of the user.

Optionally, the processing module 404 includes:

an inputting unit, configured to input the training feeling data of the user after each session of psychological counseling training into the first classification model, to generate an N1-dimensional vector corresponding to the training result, wherein each dimension vector in the N1-dimensional vector corresponds to one category of training feeling data, and each dimension vector indicates a training feeling level of the user by using a number;

a first generation unit, configured to perform same-position accumulation on N1-dimensional vectors corresponding to multiple training results of the user in the first training period when the user has completed multiple sessions of psychological counseling training in a first training period, to generate an N2-dimensional vector corresponding to the training result of the user in the first training period; and a second generation unit, configured to generate an (N2*M)-dimensional vector for a training result in a second training period of the user, wherein M represents a quantity of first training periods contained in each second training period.

Optionally, the processing module 404 further includes:

a first obtaining unit, configured to obtain first sample data, wherein the first sample data includes at least one of the following categories: data used to describe a post-training idea, data used to describe post-training body feelings, and data used to describe post-training emotional feeling;

a first annotation unit, configured to annotate a training feeling level of each category of the first sample data; and a first training unit, configured to train the first classification model by using the annotated first sample data, wherein different categories of first sample data are used to correspondingly train different categories of first classification models.

Optionally, the processing module 404 further includes:

a counting unit, configured to count a quantity of training sessions of the user that are completed in the second training period, to serve as an (N2*M+1)-dimensional vector.

Optionally, the determining module 406 includes:

a second obtaining unit, configured to obtain, through an interactive inquiry with the user, a feedback result of the user after the current second training period ends;

a first determining unit, configured to determine a training scheme of the user for a next second training period according to a preset training procedure when the feedback result of the user indicates that expected effects are achieved; and a second determining unit, configured to input the training result in the current second training period of the user into a second classification model when the feedback result of the user indicates that expected effects are not achieved or the user does not explicitly provide feedback, and determine the training scheme of the user for the next second training period by using the second classification model, wherein the second classification model is a model obtained by training an initial classifier model.

Optionally, the second determining unit includes:

an inputting subunit, configured to input an L-dimensional vector corresponding to statistics of the user in the current second training period into the second classification model, wherein the L-dimensional vector includes an (N2*M)-dimensional vector corresponding to the training result in the current training period of the user or an (N2*M+1)-dimensional vector corresponding to the training result and a quantity of training sessions of the user in the current training period;

an outputting subunit, configured to output a psychological tendency result of the user by using the second classification model, wherein the psychological tendency result is used to indicate whether the training of the user in the current second training period achieves expected effects; and a determining subunit, configured to determine the training scheme of the user for the next second training period based on the psychological tendency result of the user.

Optionally, the determining module 406 further includes:

a third obtaining unit, configured to obtain second sample data composed of an L-dimensional vector corresponding to statistics of the user in one second training period;

a second annotation unit, configured to annotate a psychological tendency result corresponding to the second sample data, wherein the psychological tendency result includes at least one of the following: satisfaction and dissatisfaction; and a second training unit, configured to train the second classification model by using the annotated second sample data.

Optionally, the determining module 406 further includes:

a fourth obtaining unit, configured to obtain a target L-dimensional vector corresponding to statistics of the user in the current second training period;

a third annotation unit, configured to annotate a psychological tendency result corresponding to the target L-dimensional vector as satisfaction; and an updating unit, configured to input the annotated L-dimensional vector into the second classification model for training, and update the second classification model.

Figure 5:
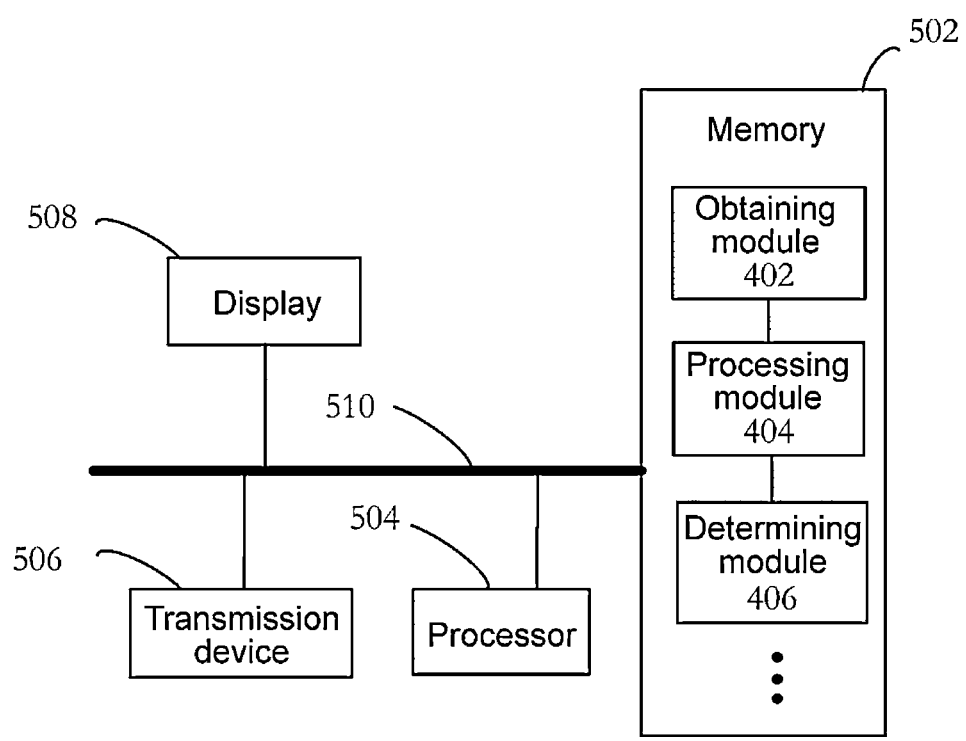
FIG. 5 is a schematic structural diagram of an optional electronic device according to an embodiment of the present disclosure.

According to still another aspect of an embodiment of the present disclosure, an electronic device for implementing the foregoing method for determining a psychological counseling training scheme is further provided. The electronic device may be, but is not limited to be applied to a server. As shown in FIG. 5, the electronic device includes a memory 502 and a processor 504. The memory 502 stores a computer program. The processor 504 is configured to execute the steps in any one of the foregoing method embodiments through the computer program.

Optionally, in this embodiment, the electronic device may be located in at least one of a plurality of network devices in a computer network.

Optionally, in this embodiment, the processor may be configured to perform the following steps through the computer program:

S1: obtaining training feeling data of a user after each session of psychological counseling training through an interactive inquiry with the user, wherein the training feeling data is used to indicate feeling of the user after the psychological counseling training;

S2: inputting the training feeling data into a first classification model, identifying a training result of the user after each session of psychological counseling training by using the first classification model, and collecting statistics about a training result of the user in a current training period, wherein the first classification model is a model obtained by training an initial ultra-long text classification model; and S3: determining a training scheme of the user for a next training period based on the training result in the current training period of the user.

Optionally, a person skilled in the art may understand that the structure shown in FIG. 5 is only for example, and the electronic device may also be a terminal device such as a smart phone (such as an Android phone or an iOS phone), a tablet computer, a palmtop computer, a mobile internet device (MID), or a PAD. FIG. 5 does not constitute a limitation on a structure of the foregoing electronic device. For example, the electronic device may further include more or less components (such as network interfaces) than those shown in FIG. 5, or may have a configuration different from that shown in FIG. 5.

The memory 502 may be configured to store software programs and modules, such as program instructions/modules corresponding to the method and apparatus for determining a psychological counseling training scheme in the embodiments of the present disclosure. The processor 504 runs the software programs and modules stored in the memory 502 to perform various function applications and data processing, that is, realize the foregoing method for determining a psychological counseling training scheme. The memory 502 may include a high-speed random access memory, and may further include a non-volatile memory, such as one or more magnetic storage devices, a flash memory, or another non-volatile solid-state memory. In some embodiments, the memory 502 may further include memories remotely disposed with respect to the processor 504, and these remote memories may be connected to a terminal through a network. Examples of the foregoing network include, but are not limited to, the internet, an intranet, a local area network, a mobile communications network, and combinations thereof. The memory 502 may be specifically, but is not limited to be configured to store program steps of the method for determining a psychological counseling training scheme. As an example, as shown in FIG. 5, the foregoing memory 502 may include, but is not limited to the obtaining module 402, the processing module 404, the determining module 406, and the like in the foregoing apparatus for determining a psychological counseling training scheme. In addition, the memory 502 may further include, but is not limited to other module units in the foregoing apparatus for determining a psychological counseling training scheme. Details are not described in this example.

Optionally, the transmission device 506 is configured to receive or send data through a network. Specific examples of the foregoing network may include a wired network and a wireless network. In an example, the transmission device 506 includes a network interface controller (NIC), which can be connected to another network device and router through a network cable, to communicate with the internet or a local area network. In an example, the transmission device 506 is a radio frequency (RF) module, and is configured to communicate with the internet in a wireless manner.

In addition, the foregoing electronic device further includes: a display 508, configured to display alarm push of a suspicious account; and a connection bus 510, configured to connect various module components in the foregoing electronic device.

An embodiment of the present disclosure further provides a computer-readable storage medium. The storage medium stores a computer program, and the computer program is configured to implement the steps in any one of the foregoing method embodiments while being executed.

Optionally, in this embodiment, the storage medium may be configured to store the computer program that is configured to perform following steps:

S1: obtaining training feeling data of a user after each session of psychological counseling training through an interactive inquiry with the user, wherein the training feeling data is used to indicate feeling of the user after the psychological counseling training;

S2: inputting the training feeling data into a first classification model, identifying a training result of the user after each session of psychological counseling training by using the first classification model, and collecting statistics about a training result of the user in a current training period, wherein the first classification model is a model obtained by training an initial ultra-long text classification model; and S3: determining a training scheme of the user for a next training period based on the training result in the current training period of the user.

Optionally, the storage medium is further configured to store a computer program that is configured to perform steps included in the method in the foregoing embodiment. Details are not described in this embodiment.

Optionally, in this embodiment, one of ordinary skills in the art may understand that all or some of the steps in various methods in the foregoing embodiments may be completed by instructing hardware related to a terminal device program through a program. The program may be stored in a computer readable storage medium. The storage medium may include: a flash drive, a read-only memory (ROM), a random access memory (RAM), a magnetic disk, or a compact disc.

Sequence numbers in the foregoing embodiments of the present disclosure are only for description, and do not represent superiority or inferiority of the embodiments.

If an integrated unit in the foregoing embodiment is implemented in a form of a software functional unit and is sold or used as an independent product, the integrated unit may be stored in the foregoing computer-readable storage medium. On the basis of such understanding, the technical solutions of the present disclosure essentially, or parts of the technical solutions of the present disclosure that contribute to the prior art, or all or part of the technical solutions may be represented in the form of software products. The computer software product may be stored in a storage medium, and includes a plurality of instructions to enable one or more computer devices (which may be a personal computer, a server, a network device, or the like) to implement all or some steps of the method in all embodiments of the present disclosure.

In the foregoing embodiments of the present disclosure, the description of each embodiment has its own focus. For parts that are not described in detail in an embodiment, reference may be made to related descriptions of other embodiments.

In the embodiments provided in the present disclosure, it should be understood that the disclosed client may be implemented in other manners. The device embodiments described above are merely exemplary. For example, the division of units is only a division of logical functions. In actual implementations, there may be other division manners. For example, a plurality of units or components may be combined or may be integrated into another system, or some features may be ignored or not implemented. In addition, the displayed or discussed mutual coupling or direct coupling or communications connection may be indirect coupling or communication connections through some interfaces, devices, or units, and may be in electrical or other forms.

The units described as separated parts may be or may not be physically separated; and parts displayed as units may be or may not be physical unit, that is, may be located at one place or may be distributed on a plurality of network units. Some or all of the units may be selected according to actual requirements to achieve the objectives of the solutions of the embodiments.

In addition, all functional units in the embodiments of the present disclosure may be integrated into one processing unit, or each unit may exist alone physically, or two or more units may be integrated into one unit. The foregoing integrated unit may be implemented in a form of hardware, or may be implemented in a form of a software function unit.

The preferred implementations of the present disclosure are described above. It should be noted that for persons of ordinary skills in the art, improvements and modifications can be made without departing from the principles of the present disclosure, and these improvements and modifications should also be considered as being subject to the protection scope of the present disclosure.

What is claimed is:

1. A method for determining a psychological counseling training scheme, comprising:

obtaining training feeling data of a user after each session of psychological counseling training through an interactive inquiry with the user, wherein the training feeling data is used to indicate feeling of the user after the psychological counseling training;

inputting the training feeling data into a first classification model, identifying a training result of the user after each session of psychological counseling training by using the first classification model, and collecting statistics about a training result of the user in a current training period, wherein the first classification model is a model obtained by training an initial ultra-long text classification model; and determining a training scheme of the user for a next training period based on the training result in the current training period of the user, wherein the inputting the training feeling data into a first classification model, identifying a training result of the user after each session of psychological counseling training by using the first classification model, and collecting statistics about a training result of the user in a current training period comprises:

inputting the training feeling data of the user after each session of psychological counseling training into the first classification model to generate an N1-dimensional vector corresponding to the training result, wherein each dimension vector in the N1-dimensional vector corresponds to one category of training feeling data, and each dimension vector indicates a training feeling level of the user by using a number;

performing same-position accumulation on N1-dimensional vectors corresponding to multiple training results of the user in the first training period when the user has completed multiple sessions of psychological counseling training in a first training period, to generate an N2-dimensional vector corresponding to the training result of the user in the first training period; and generating an (N2*M)-dimensional vector for a training result in a second training period of the user, wherein M represents a quantity of first training periods contained in each second training period.

2. The method according to claim 1, wherein before the inputting the training feeling data of the user after each session of psychological counseling training into the first classification model to generate an N1-dimensional vector corresponding to the training result, the method further comprises:

obtaining first sample data, wherein the first sample data comprises at least one of the following categories: data used to describe a post-training idea, data used to describe post-training body feelings, and data used to describe post-training emotional feeling;

annotating a training feeling level of each category of the first sample data; and training the first classification model by using the annotated first sample data, wherein different categories of first sample data are used to correspondingly train different categories of first classification models.

3. The method according to claim 1, wherein after the generating an (N2*M)-dimensional vector for a training result in a second training period of the user, the method further comprises:

counting a quantity of training sessions of the user that are completed in the second training period to serve as an (N2*M+1)-dimensional vector.

4. The method according to claim 3, wherein the determining a training scheme in a next training period of the user based on the training result in the current training period of the user comprises:

obtaining a feedback result of the user after the current second training period ends through an interactive inquiry with the user;

determining a training scheme of the user for a next second training period according to a preset training procedure when the feedback result of the user indicates that expected effects are achieved; and inputting the training result in the current second training period of the user into a second classification model when the feedback result of the user indicates that expected effects are not achieved or the user does not explicitly provide feedback, and determining the training scheme of the user for the next second training period by using the second classification model, wherein the second classification model is a model obtained by training an initial classifier model.

5. The method according to claim 4, wherein the determining the training scheme of the user for a next second training period by using the second classification model comprises:

inputting an L-dimensional vector corresponding to statistics of the user in the current second training period into the second classification model, wherein the L-dimensional vector comprises an (N2*M)-dimensional vector corresponding to the training result in the current training period of the user or an (N2*M+1)-dimensional vector corresponding to the training result and a quantity of training sessions of the user in the current training period;

outputting a psychological tendency result of the user by using the second classification model, wherein the psychological tendency result is used to indicate whether the training of the user in the current second training period achieves expected effects; and determining the training scheme of the user for the next second training period based on the psychological tendency result of the user.

6. The method according to claim 5, wherein before the determining the training scheme of the user for a next second training period by using the second classification model, the method further comprises:

obtaining second sample data composed of an L-dimensional vector corresponding to statistics of the user in one second training period;

annotating a psychological tendency result corresponding to the second sample data, wherein the psychological tendency result comprises at least one of the following: satisfaction and dissatisfaction; and training the second classification model by using the annotated second sample data.

7. The method according to claim 6, wherein when the feedback result of the user indicates that expected effects are achieved, the method further comprises:

obtaining a target L-dimensional vector corresponding to statistics of the user in the current second training period;

annotating a psychological tendency result corresponding to the target L-dimensional vector as satisfaction; and inputting the annotated target L-dimensional vector into the second classification model for training, and updating the second classification model.

8. An apparatus for determining a psychological counseling training scheme, comprising:

an obtaining module, configured to obtain training feeling data of a user after each session of psychological counseling training through an interactive inquiry with the user, wherein the training feeling data is used to indicate feeling of the user after the psychological counseling training;

a processing module, configured to input the training feeling data into a first classification model, identify a training result of the user after each session of psychological counseling training by using the first classification model, and collect statistics about a training result of the user in a current training period, wherein the first classification model is a model obtained by training an initial ultra-long text classification model; and a determining module, configured to determine a training scheme of the user for a next training period based on the training result in the current training period of the user, wherein the processing module is further configured to:

input the training feeling data of the user after each session of psychological counseling training into the first classification model to generate an N1-dimensional vector corresponding to the training result, wherein each dimension vector in the N1-dimensional vector corresponds to one category of training feeling data, and each dimension vector indicates a training feeling level of the user by using a number;

perform same-position accumulation on N1-dimensional vectors corresponding to multiple training results of the user in the first training period when the user has completed multiple sessions of psychological counseling training in a first training period, to generate an N2-dimensional vector corresponding to the training result of the user in the first training period; and generate an (N2*M)-dimensional vector for a training result in a second training period of the user, wherein M represents a quantity of first training periods contained in each second training period.

9. A computer-readable storage medium, wherein the storage medium stores a computer program, and the computer program is configured to perform the method according to claim 1 while being executed.

10. An electronic device, comprising a memory and a processor, wherein the memory stores a computer program, and the processor is configured to execute the computer program to perform the method according to claim 1.

* * * * *